United States Patent
Perrey et al.

(10) Patent No.: US 10,679,753 B2
(45) Date of Patent: Jun. 9, 2020

(54) METHODS AND SYSTEMS FOR HIERARCHICAL MACHINE LEARNING MODELS FOR MEDICAL IMAGING

(71) Applicant: General Electric Company, Schenectady, NY (US)

(72) Inventors: Christian Fritz Perrey, Mondsee (AT); Nitin Singhal, Bangalore (IN)

(73) Assignee: General Electric Company, Schenectady, NY (US)

( * ) Notice: Subject to any disclaimer, the term of this patent is extended or adjusted under 35 U.S.C. 154(b) by 206 days.

(21) Appl. No.: 15/900,386

(22) Filed: Feb. 20, 2018

(65) Prior Publication Data

US 2018/0240551 A1 Aug. 23, 2018

(30) Foreign Application Priority Data

Feb. 20, 2017 (IN) .............................. 201741005869

(51) Int. Cl.
| | | |
|---|---|---|
| *G16H 50/20* | (2018.01) | |
| *G16H 30/20* | (2018.01) | |
| *G16H 30/40* | (2018.01) | |
| *G06N 20/00* | (2019.01) | |
| *G06N 5/00* | (2006.01) | |

(52) U.S. Cl.
CPC ............. *G16H 50/20* (2018.01); *G16H 30/20* (2018.01); *G16H 30/40* (2018.01); *G06N 5/003* (2013.01); *G06N 20/00* (2019.01)

(58) Field of Classification Search
CPC ....... G06T 7/0012; A61B 8/48; A61B 8/5215; G16H 30/40; G16H 50/20
See application file for complete search history.

(56) References Cited

U.S. PATENT DOCUMENTS

2015/0173705 A1* 6/2015 Lee et al. .............. A61B 8/0825
  600/407
2016/0364862 A1* 12/2016 Reicher et al. ......... G06F 19/00

* cited by examiner

*Primary Examiner* — Andrew W Johns (57) ABSTRACT

Systems and methods are provided relating to hierarchical machine learning models to identify an anatomical structure of interest and perform diagnostic procedures for a medical diagnostic imaging system. The systems and methods organize a plurality of models into a hierarchical structure based on anatomical structures. The plurality of models are defined by a machine learning algorithm for diagnostic procedures of one or more of the anatomical structures. The systems and methods receive a medical image, identifying an anatomical structure of interest within the medical image, select at least a first model from the plurality of models based on the anatomical structure of interest, and perform a first diagnostic procedure of the anatomical structure of interest based on the first model.

20 Claims, 5 Drawing Sheets

METHODS AND SYSTEMS FOR HIERARCHICAL MACHINE LEARNING MODELS FOR MEDICAL IMAGING

FIELD

Embodiments described herein generally relate to hierarchical machine learning models to identify an anatomical structure of interest and perform diagnostic procedures for a medical diagnostic imaging system.

BACKGROUND OF THE INVENTION

A machine learning and/or deep learning frameworks involve various algorithms that define an initial model based on training data. The frameworks automatically adjust the initial model based on user feedback. Conventional frameworks cover a broad range of applications, such as organ detection, scan plane selection, segmentation and tissue classification. However, the conventional frameworks are isolated and specialized for specific applications. For example, each conventional framework is developed and trained for each application separately. During a scan and/or image analysis, one of the conventional frameworks are manually selected by the user utilizing a user interface. It would be desirable to have one machine learning and/or deep learning framework that includes all anatomical structures and applications. However, conventional frameworks would require training for all possible anatomical structures and/or user selections, which requires complex training and time to implement.

BRIEF DESCRIPTION OF THE INVENTION

A method (e.g., a computer implemented method) is provided. The method includes organizing a plurality of models into a hierarchical structure based on anatomical structures. The plurality of models are defined by a machine learning algorithm for diagnostic procedures of one or more of the anatomical structures. The method includes receiving a medical image, identifying an anatomical structure of interest within the medical image, selecting at least a first model from the plurality of models based on the anatomical structure of interest, and performing a first diagnostic procedure of the anatomical structure of interest based on the first model.

A system (e.g., a medical diagnostic imaging system) is provided. The system includes a display configured to display one or more medical images and a controller circuit. The controller circuit configured to organize a plurality of models into a hierarchical structure based on anatomical structures. The plurality of models are defined by a machine learning algorithm for diagnostic procedures of one or more of the anatomical structures. The controller circuit is further configured to receive a medical image, identify an anatomical structure of interest within the medical image, select at least a first model from the plurality of models based on the anatomical structure of interest, and perform a first diagnostic procedure of the anatomical structure of interest based on the first model.

A tangible and non-transitory computer readable medium is provided. The tangible and non-transitory computer readable medium includes one or more programmed instructions configured to direct one or more processors. The programmed instructions direct the one or more processors to organize a plurality of models into a hierarchical structure based on anatomical structures. The plurality of models are defined by a machine learning algorithm for diagnostic procedures of one or more of the anatomical structures. The programmed instructions further direct the one or more processors to receive a medical image, identify an anatomical structure of interest within the medical image, select at least a first model from the plurality of models based on the anatomical structure of interest, and perform a first diagnostic procedure of the anatomical structure of interest based on the first model.

DETAILED DESCRIPTION OF THE INVENTION

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments described herein generally relate to hierarchical machine learning models to identify an anatomical structure of interest and perform diagnostic procedures for a medical diagnostic imaging system. For example, a medical diagnostic system is provided herein. The medical diagnostic system includes a plurality of models based on machine learning and/or deep learning frameworks. Each of the models may correspond to a diagnostic procedure of one or more anatomical structures. The diagnostic procedure may include at least one of identifying a two-dimensional plane, segmenting the anatomical structure of interest, measuring a boundary thickness of the anatomical structure of interest, measuring a volume of the anatomical structure of interest, identifying the anatomical structure within the medical image, annotating objects within the medical image, measuring an area of the anatomical structure of interest, and/or the like. The models are organized in a hierarchical manner, such as, organized into a hierarchical structure based on anatomical structures based on the diagnostic procedure of the models.

For example, the medical diagnostic system is configured to perform an image analysis on a medical image in a hierarchical fashion by utilizing a top down approach to identify an anatomical structure within the medical image. The medical image may be an ultrasound image, a CT image, a PET image, an MRI image, an x-ray image, or an image acquired through another imaging modality by a medical diagnostic imaging system. The anatomical structure may be an organ (e.g., heart, kidney, bladder, lung, brain, and/or the like), skeletal structure (e.g., bone, skull, and/or the like), vascular structure (e.g., artery, vein, and/or the like), region of body (e.g., head, torso, and/or the like), and/or the like. The medical diagnostic system may identify the anatomical structure, for example, utilizing a machine learning algorithm. Based on the identified anatomical structure, one or more of the plurality of models representing specialized diagnostic procedures are manually and/or automatically selected for subsequent analysis of the anatomical structure within the medical image. It may be noted that the medical diagnostic system may be configured to performed the operations described herein during a scan and/or offline (e.g., after scanning utilizing stored one or more medical images).

A technical effect of at least one embodiment described herein reduces clinician variability between different image analyses. A technical effect of at least one embodiment described herein reduces user interaction and analysis time. A technical effect of at least one embodiment described herein enables a less experienced users to achieve consistent scan quality and reproducible results. A technical effect of at least one embodiment described herein provides guided subsequent analysis.

Figure 1A:
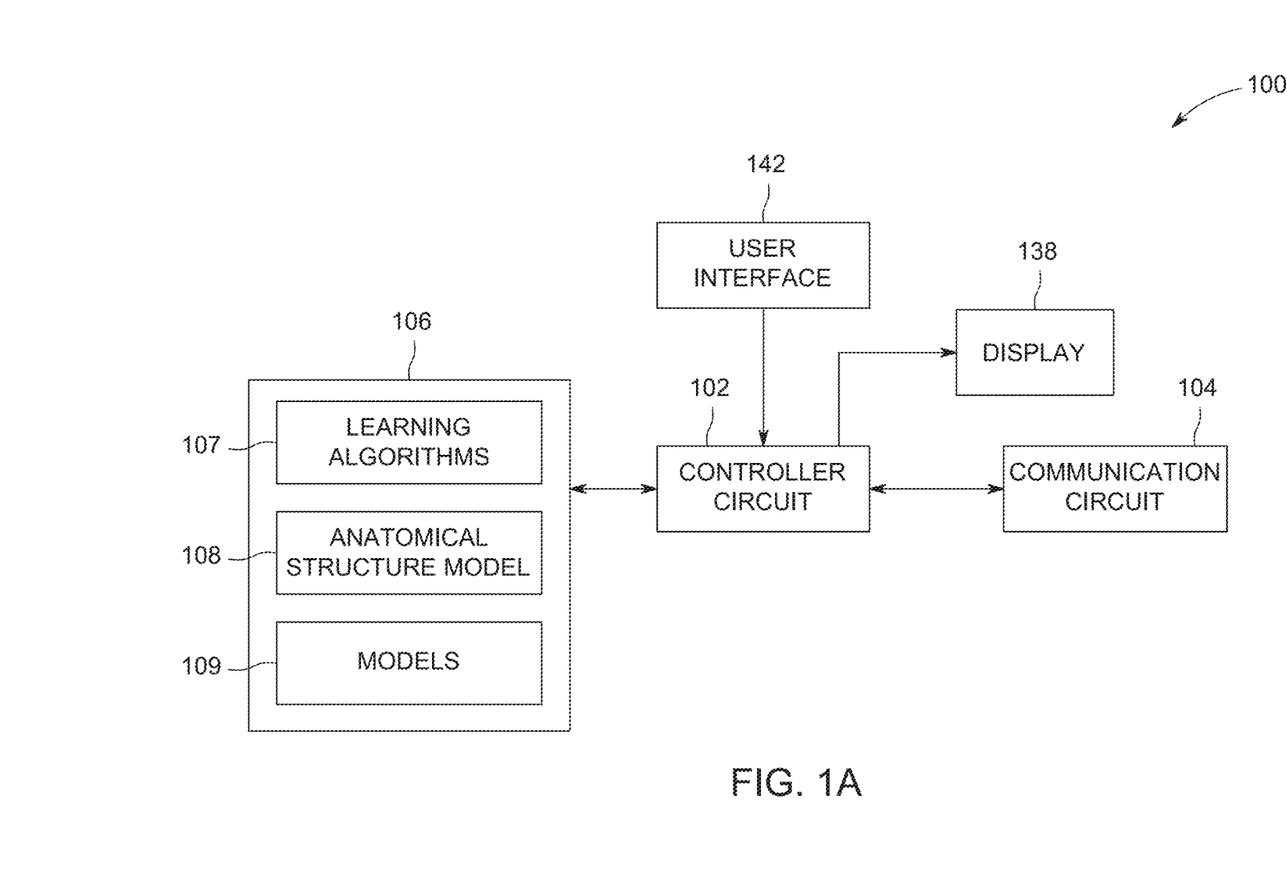
FIGS. 1A-B illustrate schematic block diagrams of various embodiments of a medical diagnostic system.
Figure 1B:
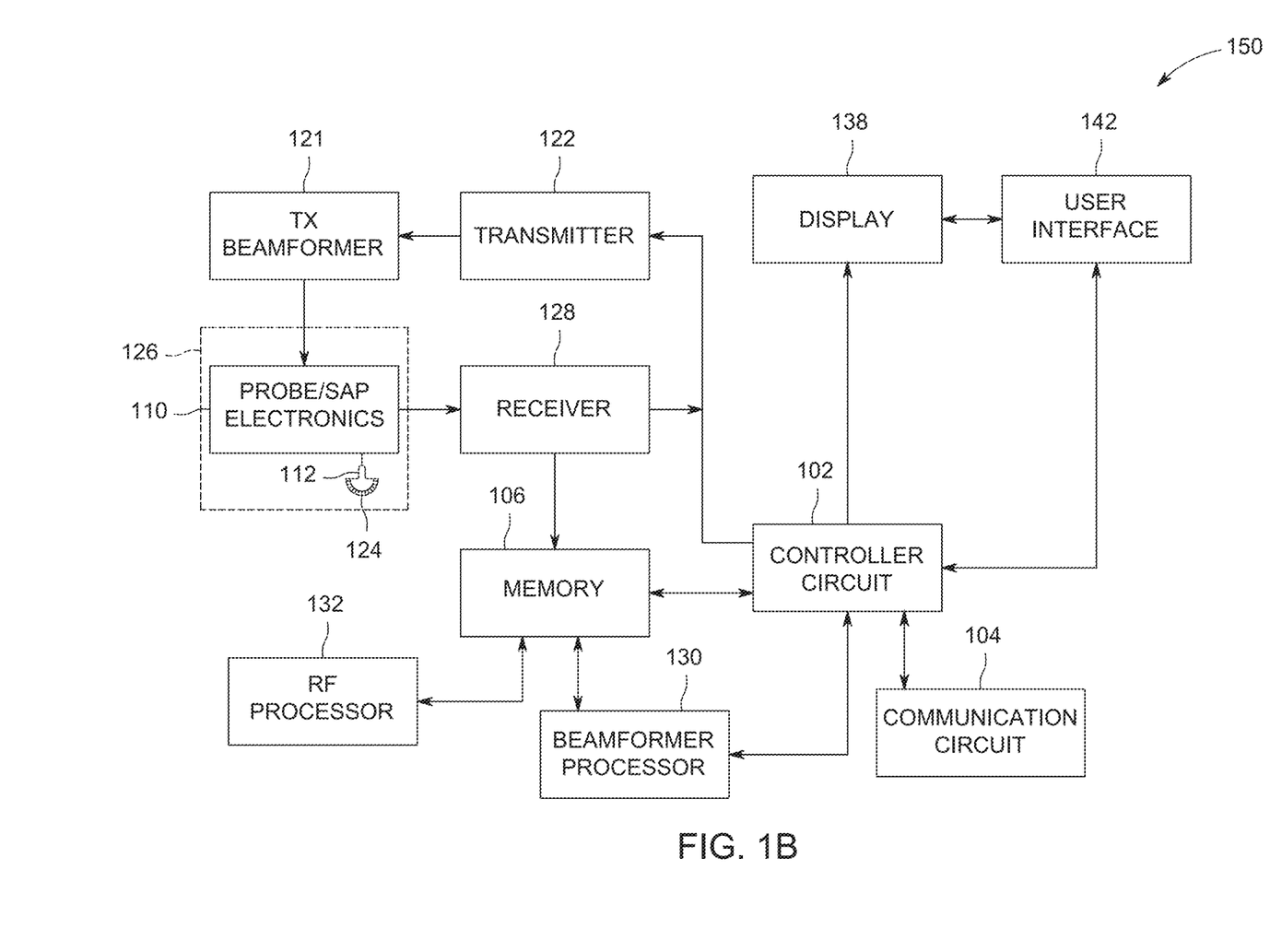

FIGS. 1A-B illustrate schematic block diagrams of various embodiments of a medical diagnostic system (MDS) 100, 150. The MDS 100 of FIG. 1A may include a controller circuit 102 operably coupled to a communication circuit 104, a display 138, a user interface 142 and a memory 106.

The communication circuit 104 may be communicatively coupled to one or more alternative MDS (e.g., such as the MDS 150 shown in FIG. 1B), one or more medical diagnostic imaging systems, a remote server, and/or the like via corresponding bi-directional communication links. The one or more medical diagnostic imaging systems may include ultrasound imaging systems or devices, nuclear medicine imaging devices (e.g., Positron Emission Tomography (PET) or Single Photon Emission Computed Tomography (SPECT) imaging systems), Magnetic Resonance (MR) imaging devices, Computed Tomography (CT) imaging devices, and/or x-ray imaging devices, and/or the like. The remote server may be configured to store sets of medical images from prior scanning and/or clinician sessions of a patient acquired by the one or more medical diagnostic imaging systems.

The bi-directional communication links may be a wired (e.g., via a physical conductor) and/or wireless communication (e.g., utilizing radio frequency (RF)) link for exchanging data (e.g., data packets) between the MDS 100 and the alternative MDS, the one or more medical diagnostic imaging systems, the remote server, and/or the like. For example, the MDS 100 may receive a set of medical images from saved scanning and/or clinician sessions from the alternative MDS, the one or more medical diagnostic imaging systems, the remote server, and/or the like. The bi-directional communication links may be based on a standard communication protocol, such as Ethernet, TCP/IP, WiFi, 802.11, a customized communication protocol, and/or the like.

The controller circuit 102 is configured to control the operation of the MDS 100. The controller circuit 102 may include one or more processors. Optionally, the controller circuit 102 may include a central controller circuit (CPU), one or more microprocessors, a graphics controller circuit (GPU), or any other electronic component capable of processing inputted data according to specific logical instructions. Optionally, the controller circuit 102 may include and/or represent one or more hardware circuits or circuitry that include, are connected with, or that both include and are connected with one or more processors, controllers, and/or other hardware logic-based devices. Additionally or alternatively, the controller circuit 102 may execute instructions stored on a tangible and non-transitory computer readable medium (e.g., the memory 106).

The controller circuit 102 may be operably coupled to and/or control a communication circuit 104. The communication circuit 104 is configured to receive and/or transmit information with the one or more medical diagnostic imaging systems, the alternative MDS, the remote server, and/or the like. The communication circuit 104 may represent hardware that is used to transmit and/or receive data along the bi-directional communication links. The communication circuit 104 may include a transceiver, receiver, transceiver and/or the like and associated circuitry (e.g., antennas) for wired and/or wirelessly communicating (e.g., transmitting and/or receiving) with the one or more medical diagnostic imaging systems, the alternative MDS, the remote server, and/or the like. For example, protocol firmware may be stored in the memory 106, which is accessed by the controller circuit 102. The protocol firmware provides the network protocol syntax for the controller circuit 102 to assemble data packets, establish and/or partition data received along the bi-directional communication links, and/or the like.

The controller circuit 102 is operably coupled to the display 138 and the user interface 142. The display 138 may include one or more liquid crystal displays (e.g., light emitting diode (LED) backlight), organic light emitting diode (OLED) displays, plasma displays, CRT displays, and/or the like. The display 138 may display patient information, one or more medical images and/or videos, components of a graphical user interface, one or more 2D, 3D, or 4D ultrasound image data sets from ultrasound data stored in the memory 106 or currently being acquired, measurements, diagnosis, treatment information, and/or the like received by the display 138 from the controller circuit 102.

The user interface 142 controls operations of the controller circuit 102 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller circuit 102, which is shown on the display 138. The touch screen display can detect a presence of a touch from the operator on the display 138 and can also identify a location of the touch with respect to a surface area of the display 138. For example, the user may select one or more user interface icons of the GUI shown on the display by touching or making contact with the display 138. The touch may be applied by, for example, at least one of an individual's hand, glove, stylus, or the like.

The memory 106 includes parameters, algorithms, models, data values, and/or the like utilized by the controller circuit 102 to perform one or more operations described herein. The memory 106 may be a tangible and non-transitory computer readable medium such as flash memory, RAM, ROM, EEPROM, and/or the like. The memory 106 may include a set of machine learning algorithms 107 (e.g., convolutional neural network algorithms, deep learning algorithms, decision tree learning algorithms, and/or the like) configured to define a plurality of models 109 and an anatomical structure model 108. Additionally or alternatively, the models 109 and/or the anatomical structure model 108 may be received along one of the bi-directional communication links via the communication circuit 104 and stored in the memory 106.

For example, the anatomical structure model 108 may be defined by the machine learning algorithms 107 to identify one or more anatomical structures of interest based on features of the one or more anatomical structures (e.g., boundaries, thickness, and/or the like) within the one or more medical images. The features may represent high level features of the pixels and/or voxels of the medical image such as a histogram orient gradients, blob features, covariance features, binary pattern features, and/or the like. Optionally, the machine learning algorithm 107 may define the anatomical structure model 108 by automatically building a statistical model and/or a database of true positives and true negatives corresponding to each anatomical structure identified based on the features from a set of training images, a classification model, supervised modeling, and/or the like.

For example, the anatomical structure model 108 may be configured and/or designed based on a plurality of training medical images. The plurality of training images may be grouped into different anatomical structure sets, such as organs (e.g., heart, kidney, liver, bladder, lung, brain, and/or the like), skeletal structures (e.g., bone, skull, and/or the like), vascular structures (e.g., artery, vein, and/or the like), regions of a body (e.g., head, torso, and/or the like), and/or the like. Additionally or alternatively, the training images within each set may represent different orientations and/or views of the one or more anatomical structures. For example, a set of the training images may include over 50,000 medical images. For example, a set of the training images may include one or more different views corresponding to the heart. In another example, a second set of the training images may include one or more different views corresponding to the brain.

Additionally or alternatively, the anatomical structure model 108 may be defined based on a supervised learning method. For example, a user (e.g., skilled medical practitioner) may manually label the one or more anatomical structures within the plurality of training medical images utilizing the user interface 142. The manually labeled medical images may be used to build a statistical model and/or a database of true positives and true negatives corresponding to each anatomical structure defining the anatomical structure model 108.

The plurality of models 109 are configured to define a diagnostic procedure for one or more anatomical structures. The diagnostic procedure may represent at least one of identifying a two-dimensional plane, segmenting the anatomical structure of interest, measuring a boundary thickness of the anatomical structure of interest, measuring a volume of the anatomical structure of interest, identifying the anatomical structure within the medical image, annotating objects within the medical image, measuring an area of the anatomical structure of interest, and/or the like. For example, the plurality of models 109 may be defined by the machine learning algorithms 107 corresponding to specific anatomical structures.

For example, at least one of the plurality of models 109 may be defined by the machine learning algorithms 107 to define a two-dimensional plane representing the mid-sagittal plane of a head (e.g., anatomical structure). The at least one model 109 may be configured to identify the mid-sagittal plane of the head defined by the machine learning algorithms 107 utilizing pattern recognition. For example, the controller circuit 102 executing the at least one model 109 is configured to identify structures within the head based on features of the head (e.g., eye socket, internal bone structure, thickness, shape, and/or the like) within the medical image. The features may be based on high level features of the pixels and/or voxels of the medical image such as a histogram orient gradients, blob features, covariance features, binary pattern features, and/or the like. Optionally, the machine learning algorithm 107 may define the at least one model 109 by automatically building a statistical model and/or a database of true positives and true negatives corresponding to each anatomical structure for the at least one model 109 identified based on the features. The controller circuit 102 executing the at least one model 109 may define a two-dimensional plane representing the mid-sagittal plane based on a symmetric plane based on the identified structures.

In another example, at least one of the plurality of models 109 may be defined by the machine learning algorithms 107 to segment a bladder (e.g., anatomical structure) from the medical image. At least one model 109 may be configured to identify the bladder defined by the machine learning algorithms 107 utilizing a classification model (e.g., random forest classifier). The machine learning algorithm 107 defines at least one model 109 based on a pixel level classifier model to label and/or assign each pixel of the medical image into a plurality of categories or classes (e.g., muscle, fat, background anatomy, bladder). The controller circuit 102 executing the classification model may determine the classes from a feature space of the pixels based from the various intensities and spatial positions of pixels within the medical image. The controller circuit 102 executing the at least one model 109 may continually select a pixel of the medical image, and compare characteristics of the select pixel to feature vectors. For example, the controller circuit 102 may compare an intensity or brightness of the select pixel to feature vectors of the classification model. In another example, the controller circuit 102 may determine a variance kurtosis, skewness, or spatial distribution characteristic of the select pixel by comparing the intensity of the select pixel with adjacent and/or proximate pixels around the select pixel.

A number of characteristics of the select pixel compared by the controller circuit 102 may be based on the feature sets included in the feature vectors. Each feature vector may be an n-dimensional vector that includes three or more features of pixels (e.g., mean, variance, kurtosis, skewness, spatial distribution) corresponding to a class (e.g., a background anatomy, muscle tissue, fat, the bladder) of pixels of anatomy within an ultrasound image. The feature vectors of the classification model may be generated and/or defined by the controller circuit 102 based on a plurality of test medical images. For example, the controller circuit 102 may select pixel blocks from one hundred reference ultrasound images. The select pixel blocks may have a length of five pixels and a width of five pixels. For example, a plurality of pixels within each select pixel block may represent and/or correspond to one of the classes, such as tissue of the bladder. Based on the plurality of pixels within the select pixel blocks, the controller circuit 102 may generate and/or define a feature vector. The controller circuit 102 may determine feature sets for each pixel within the plurality of pixels of a select pixel block or more than one select pixel block corresponding to the same class. One of the feature sets may be based on an intensity histogram of the reference ultrasound images. For example, the controller circuit 102 may calculate a mean intensity of the plurality of pixels, a variance of the plurality of pixel intensities, a kurtosis or shape of intensity distribution of the plurality of pixels, a skewness of the plurality of pixels, and/or the like.

Additionally, one of the feature sets may correspond to a position or spatial feature of the pixels within the select pixel block. A spatial positon with respect to a positon within the reference image (e.g., central location) and a depth with respect to an acquisition depth within the patient. The controller circuit 102 may perform a k-means clustering and/or random forest classification on the feature sets to define feature values that correspond to the class of the select pixel blocks. The controller circuit 102 may define a feature vector corresponding to the class based on the feature values to the classification model. The controller circuit 102 may assign a class to the select pixel based on a corresponding feature vector. When the select pixel is assigned a class, the controller circuit 102 may repeat the classification model to the remaining pixels of the medical image, thereby segmenting the bladder within the medical image.

It may be noted that the machine learning algorithms utilized to define the plurality of models 109 and/or the anatomical structure model 108 are examples, additional methods are available for a person of ordinary skill in the art.

In connection with FIG. 1B, the MDS 150 may be integrated with and/or apart of a medical diagnostic imaging system. For example, the MDS 150 includes an ultrasound imaging system. The MDS 150 includes an ultrasound probe 126 having a transmitter 122, transmit beamformer 121 and probe/SAP electronics 110. The probe/SAP electronics 110 may be used to control the switching of the transducer elements 124. The probe/SAP electronics 110 may also be used to group transducer elements 124 into one or more sub-apertures.

The ultrasound probe 126 may be configured to acquire ultrasound data or information from the anatomical structures (e.g., organ, blood vessel, heart) of the patient based on the predetermined settings of the first model. The ultrasound probe 126 is communicatively coupled to the controller circuit 102 via the transmitter 122. The transmitter 122 transmits a signal to a transmit beamformer 121 based on acquisition settings received by the controller circuit 102. The acquisition settings may define an amplitude, pulse width, frequency, gain setting, scan angle, power, time gain compensation (TGC), resolution, and/or the like of the ultrasonic pulses emitted by the transducer elements 124. The transducer elements 124 emit pulsed ultrasonic signals into a patient (e.g., a body). The acquisition settings may be defined by the user utilizing the user interface 142. The signal transmitted by the transmitter 122 in turn drives a plurality of transducer elements 124 within a transducer array 112.

The transducer elements 124 emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from the anatomical structures (e.g., heart, left ventricular outflow tract, breast tissues, liver tissues, cardiac tissues, prostate tissues, neonatal brain, embryo, abdomen, and the like) to produce echoes. The echoes are delayed in time and/or frequency according to a depth or movement, and are received by the transducer elements 124 within the transducer array 112. The ultrasonic signals may be used for imaging, for generating and/or tracking shear-waves, for measuring changes in position or velocity within the anatomic structure, differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored in memory 106, temporarily. The digitized signals correspond to the backscattered waves receives by each transducer element 124 at various times. After digitization, the signals still may preserve the amplitude, frequency, phase information of the backscatter waves.

Optionally, the controller circuit 102 may retrieve the digitized signals stored in the memory 106 to prepare for the beamformer processor 130. For example, the controller circuit 102 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 106) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or apart of the controller circuit 102. For example, the operations described being performed by the beamformer processor 130 may be configured to be performed by the controller circuit 102.

The beamformer processor 130 performs beamforming on the digitized signals of transducer elements and outputs a radio frequency (RF) signal. The RF signal is then provided to an RF processor 132 that processes the RF signal. The RF processor 132 may include one or more processors. Optionally, the RF processor 132 may include a central controller circuit (CPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 106). Optionally, the RF processor 132 may be integrated with and/or apart of the controller circuit 102. For example, the operations described being performed by the RF processor 132 may be configured to be performed by the controller circuit 102.

The RF processor 132 may generate different ultrasound image data types, e.g. B-mode, color Doppler (velocity/power/variance), tissue Doppler (velocity), and Doppler energy, for multiple scan planes or different scanning patterns based on the predetermined settings of the first model. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, in the memory 106.

Alternatively, the RF processor 132 may include a complex demodulator (not shown) that demodulates the RF signal to form IQ data pairs representative of the echo signals. The RF or IQ signal data may then be provided directly to the memory 106 for storage (e.g., temporary storage). Optionally, the output of the beamformer processor 130 may be passed directly to the controller circuit 102.

The controller circuit 102 may be configured to adjust the system settings, image presentation settings, and/or anatomical structures represented by the ultrasound data and/or ultrasound images acquired by the MDS 150. For example, the controller circuit 102 may be configured to process the acquired ultrasound data (e.g., RF signal data or IQ data pairs) and prepare and/or generate frames of ultrasound image data representing the anatomical structure for display on the display 138. Acquired ultrasound data may be processed in real-time by the controller circuit 102 during a scanning or therapy session as the echo signals are received. Additionally or alternatively, the ultrasound data may be stored temporarily in the memory 106 during a scanning session and processed in less than real-time in a live or off-line operation.

The memory 106 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions, and/or the like. The memory 106 may store 3D ultrasound image data sets of the ultrasound data, where such 3D ultrasound image data sets are accessed to present 2D and 3D images. For example, a 3D ultrasound image data set may be mapped into the corresponding memory 106, as well as one or more reference planes. The processing of the ultrasound data, including the ultrasound image data sets, may be based in part on user inputs, for example, user selections received at the user interface 142.

Figure 2:
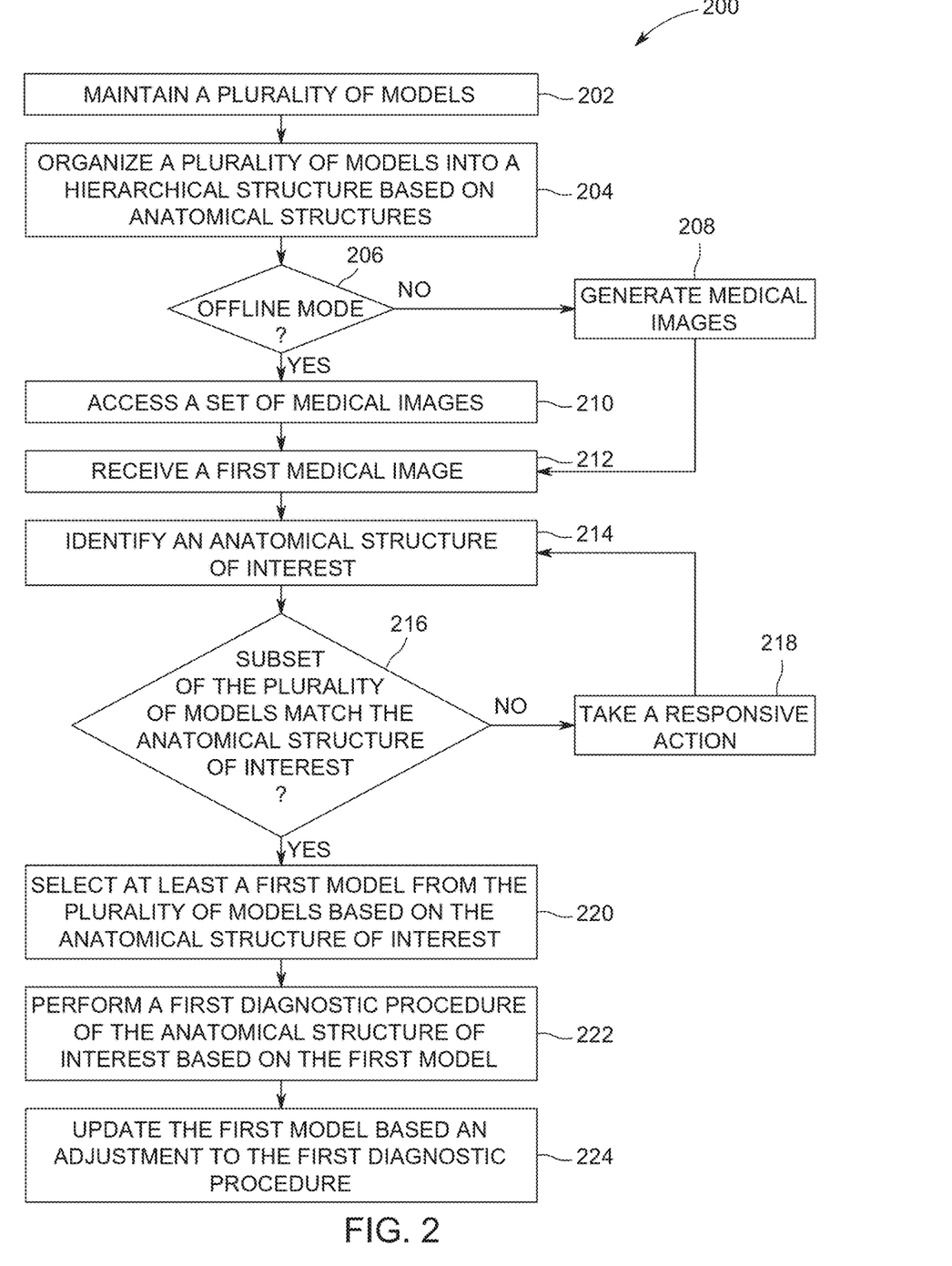
FIG. 2 illustrates a flowchart of an embodiment of a method for a computer implemented image analysis.

FIG. 2 is a flowchart of an embodiment of a method 200 for computer implemented image analysis. The method 200, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms to direct hardware to perform one or more operations described herein.

Beginning at 202, the MDS 100, 150 is configured to maintain the plurality of models 109. For example, the memory 106 of the MDS 100, 150 stores the plurality of models 109 in the memory 106, which is utilized by the controller circuit 102. Additionally or alternatively, as further described at 224, the controller circuit 102 is configured to update and/or adjust the plurality of models 109 based on user feedback received from the user interface 142.

Figure 3:
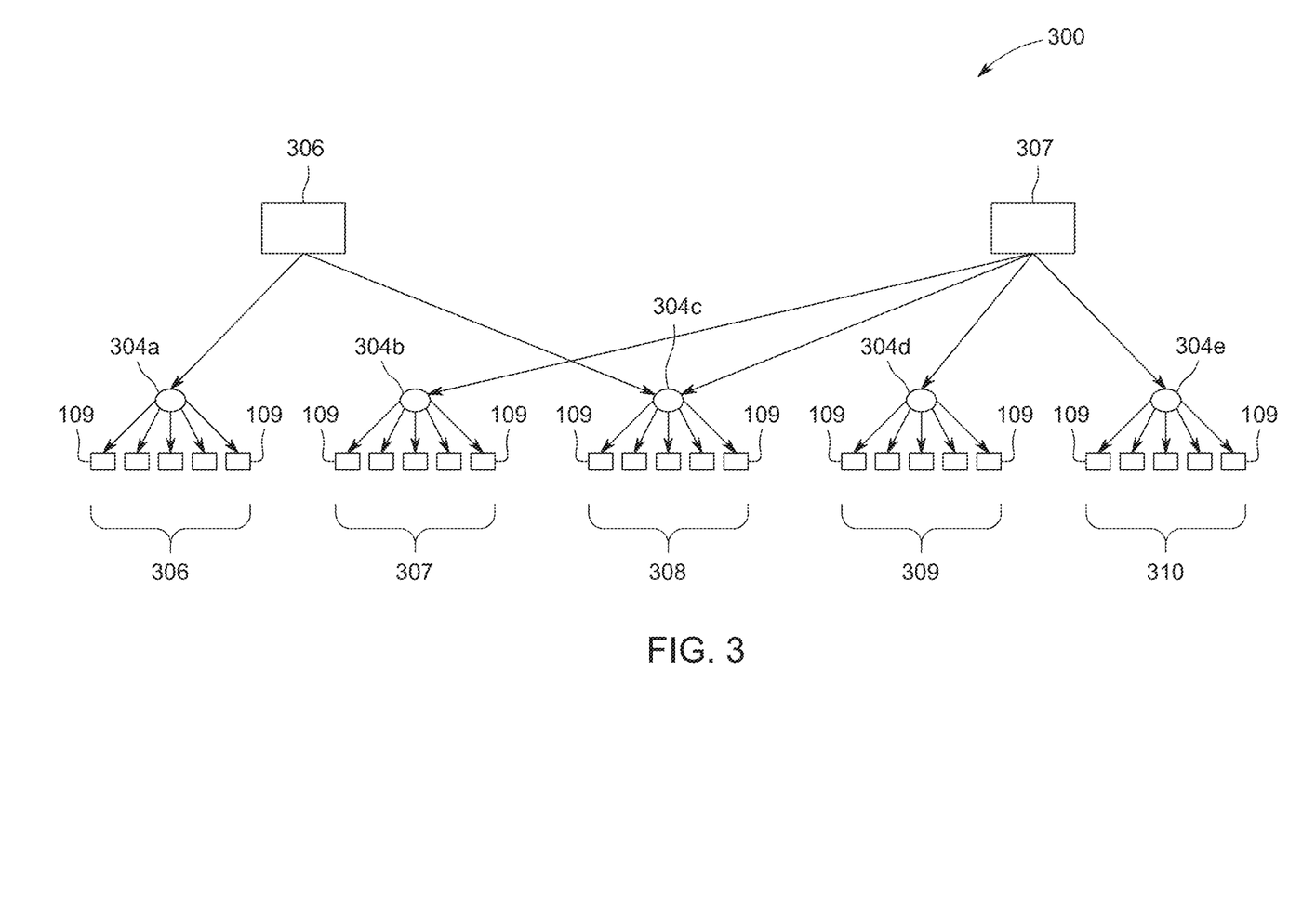
FIG. 3 illustrates a schematic block diagram of a hierarchical structure of a plurality of models, in accordance with an embodiment.

At 204, the controller circuit 102 is configured to organize the plurality of models 109 into a hierarchical structure 300 based on anatomical structures 304a-e, 306, 307 (FIG. 3). Optionally, the hierarchical structure 300 may be a visual representation of a data structure of the plurality of models 109 in the memory 106.

FIG. 3 illustrates a schematic block diagram of the hierarchical structure 300 of a plurality of models 109, in accordance with an embodiment. Each of the plurality of models 109 are grouped 306-310 based on the anatomical structure 304a-e corresponding to the diagnostic procedure executed by the plurality of models 109. The hierarchical structure 300 is configured to assign and/or link each group 306-310 to the corresponding anatomical structure 304a-e. The anatomical structures 304a-e are linked to corresponding models 109 that are defined by the machine learning algorithms 107 based on the anatomical structure 304a-e. For example, the group 306 may have diagnostic procedures corresponding to the anatomical structure 304a, representing the brain. In another example, the group 307 may have diagnostic procedures corresponding to the anatomical structure 304b, representing the liver. In another example, the group 308 each have diagnostic procedures corresponding to the anatomical structure 304c, representing bone. In another example, the group 309 each have diagnostic procedures corresponding to the anatomical structure 304d, representing a lung. In another example, the group 310 each have diagnostic procedures corresponding to the anatomical structure 304e, representing a heart.

Additionally or alternatively, the hierarchical structure 300 may represent a branching hierarchy, such that one or more anatomical structures 306, 307 may include multiple anatomical structures 304a-e and multiple groups 306-310 of the plurality of models 109. For example, the anatomical structure 306 may represent a head, which includes the brain 304a and the bone 304c. In another example, the anatomical structure 307 may represent a torso, which includes the anatomical structures 304b-4 (e.g., liver, bone, lung, and heart).

At 206, the controller circuit 102 is configured to determine whether the MDS 100, 150 is operating in an offline mode. During the offline mode the controller circuit 102 is instructed to find and/or access one or more medical images in the memory 106 and/or via the communication circuit 104 along one or more bi-directional communication links. The controller circuit 102 may determine whether the MDS 100, 150 is operating in the offline mode based on one or more selections received from the user interface 142. For example, when the controller circuit 102 is instructed to access a stored and/or previously acquired medical image via one or more user selections via the user interface 142, the controller circuit 102 may determine that the MDS 100, 150 is operating in the offline mode. In another example, when the control circuit 102 receives one or more acquisition settings for the ultrasound probe 126, the controller circuit 102 may determine that the MDS 150 is not operating in the offline mode.

If the controller circuit 102 determines the MDS 100, 150 is not operating in an offline mode, then at 208, the controller circuit 102 is configured to generate medical images. For example, the controller circuit 102 may instruct the medical diagnostic imaging system to acquire an ultrasound image, a CT image, a PET image, an MRI image, an x-ray image, and/or an image acquired through another imaging modality to acquire medical image data of a patient. Based on the medical image data, the controller circuit 102 is configured to generate one or more medical images.

For example, in connection with FIG. 1B, the controller circuit 102 may instruct the transmitter 122 to generate ultrasound signals by activating a plurality of transducer elements 124 within the transducer array 112 to a region of interest that includes an anatomical structure of interest. At least a portion of the pulsed ultrasonic signals back-scatter from the region of interest to produce echoes, which is received by the ultrasound probe 126 as ultrasound data. The ultrasound data is acquired and/or processed by the controller circuit 102 to generate one or more medical images, such as the medical image 400 shown in FIG. 4.

Figure 4:
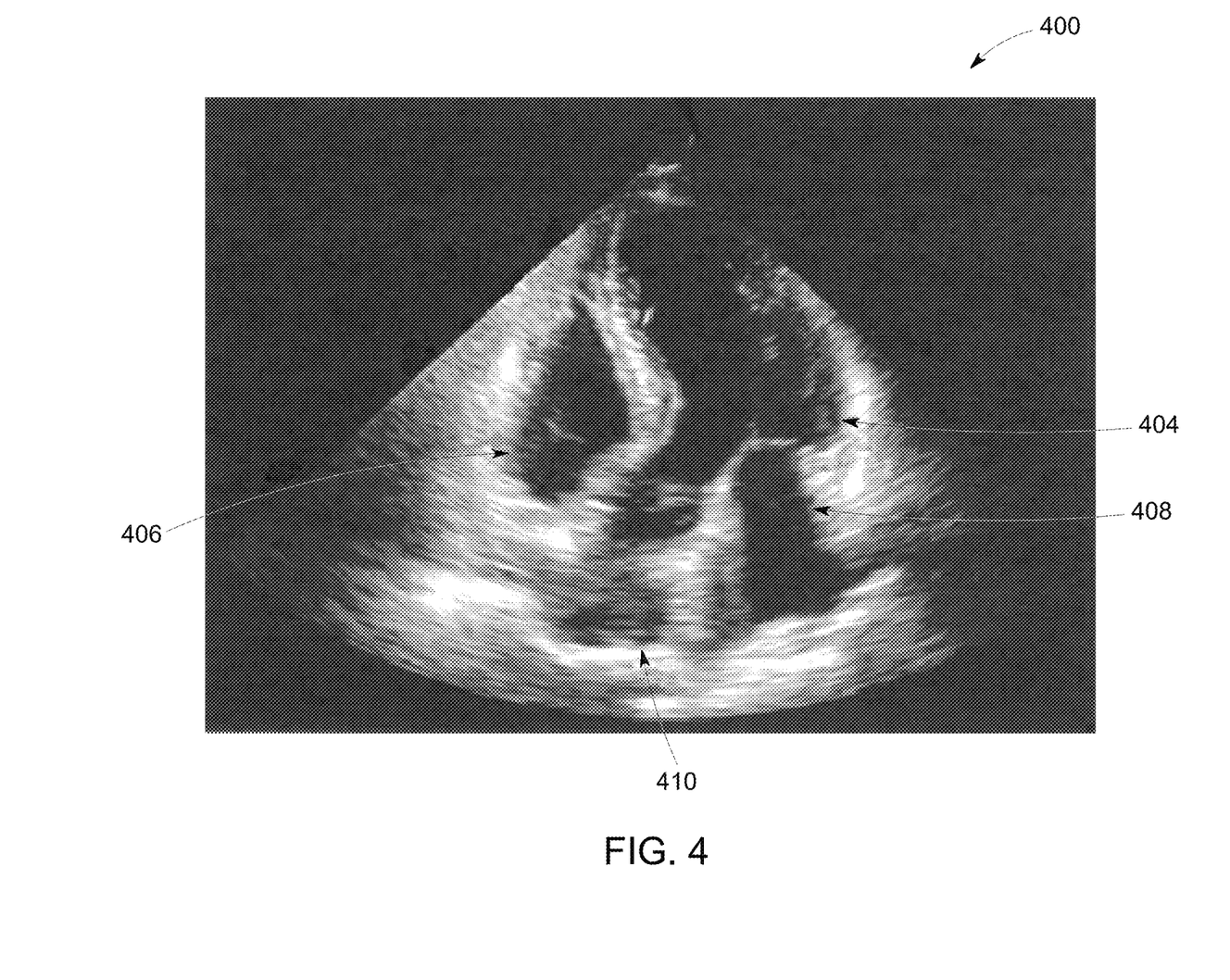
FIG. 4 illustrates a medical image of an embodiment having an anatomical structure of interest.

FIG. 4 illustrates the medical image 400 of an embodiment having an anatomical structure of interest. For example, the medical image 400 may represent a five chamber view of a heart of the patient.

If the controller circuit 102 determines the MDS 100, 150 is operating in an offline mode, then at 210, the controller circuit 102 is configured to access a set of medical images. For example, the controller circuit 102 may request an alternative MDS, a medical diagnostic imaging system, a remote server, and/or the like along a bi-directional communication link via the communication circuit 104 for a set of previously acquired medical images. Based on the request, the MDS 100, 150 may receive a set of medical images along the bi-directional communication link. Additionally or alternatively, the controller circuit 102 may access a set of medical images stored in the memory 106.

At 212, the controller circuit 102 is configured to receive a first medical image (e.g., the medical image 400). For example, the controller circuit 102 may instruct the display 138 to display a set of medical images that includes the first medical image. The user may select a first medical image and/or a subset of medical images for further image analysis by the MDS 100, 150. For example, the controller circuit 102 is configured to receive a selection of the first medical image and/or a subset of medical images from the set of medical images based on a user selection received by the user interface 142.

Additionally or alternatively, the controller circuit 102 may automatically select the first medical image. The controller circuit 102 may select one or more medical images during acquisition of the medical image data based on when the medical images were generated. For example, the controller circuit 102 may select the first medical image based on when the medical image data utilized to generate the first medical image was acquired.

At 214, the controller circuit 102 is configured to identify an anatomical structure of interest. For example, the controller circuit 102 may execute the anatomical structure model 108 defined based on the machine learning algorithm 107 using a classifier algorithm (e.g., random forest classifier), a segmentation algorithm (e.g., real time tracking contour tracking library) based on a set of training medical images (e.g., priori information), and/or the like of the first medical image, such as the medical image 400. The controller circuit 102 by executing the anatomical structure model 108 may identify individual chambers 404-410 based on changes in pixel intensities representing a heart corresponding to the anatomical structure of interest. For example, the chambers 404-410 are represented as a cluster of low intensity pixels, which are surrounded by relatively high intensity pixels (e.g., representing the septum).

At 216, the controller circuit 102 is configured to determine a subset of the plurality of models 109 that match the anatomical structure of interest. In connection with FIG. 3, the controller circuit 102 may identify the anatomical structure within the hierarchical structure 300 that matches the anatomical structure of interest identified by the controller circuit 102 executing the anatomical structure model 108. For example, the anatomical structure 304e, representing the heart, is identified by the controller circuit 102 matching the anatomical structure of interest identified within the medical image 400. Based on the anatomical structure 304e, the controller circuit 102 may determine the plurality of models 109 corresponding to the group 310.

If the controller circuit 102 determines that none of the models 109 match the anatomical structure of interest, then at 218, the controller circuit 102 is configured to take a predetermined responsive action. For example, the controller circuit 102 may transmit a request along the bi-directional communication link via the communication circuit 104 to the remote server, the alternative MSD, the medical diagnostic imaging system, and/or the like for one or more models that match the identified anatomical structure of interest. In another example, the controller circuit 102 may display an error window on the display 138 indicating there is no model 109 that matches the anatomical structure of interest.

Additionally or alternatively, the controller circuit 102 may request confirmation of the anatomical structure of interest. For example, the controller circuit 102 may instruct the GUI and/or the display 138 to display a user interface component (e.g., a text window, a graphical icon, and/or the like) representing the anatomical structure of interest identified by the controller circuit 102. The user may confirm the anatomical structure of interest to the controller circuit 102 based on a user selection of the user interface 142 with respect to the user interface component.

Optionally, the controller circuit 102 may include a user interface component (e.g., textual box, entry space, and/or the like) for the user to enter a different and/or user specified anatomical structure of interest utilizing the user interface 142. Based on the user specified anatomical structure of interest, the controller circuit 102 may adjust the anatomical structure model 108. For example, the controller circuit 102 may assign features identified from the first medical image when executing the anatomical structure model 108 to the user specified anatomical structure of interest.

If the controller circuit 102 determines the subset of the plurality of models, then at 220, the controller circuit 102 selects at least a first model from the plurality of models 109 based on the anatomical structure of interest. For example, the controller circuit 102 by executing the anatomical structure model 108 identifies the anatomical structure of interest being a heart represented as the anatomical structure 304e. The controller circuit 102 may be configured to automatically execute the at least first and/or select models from the subset of the plurality of models 109 within the group 310. For example, the controller circuit 102 may execute the at least first model based on the prior and/or continual usage by the user and/or based on the patient information.

Additionally or alternatively, the controller circuit 102 may select the at least first model based on a user selection. For example, the controller circuit 102 may display the models 109 within the group 310 based on the identified anatomical structure of interest by the controller circuit 102.

The user may select one or more of the displayed models 109 of the group 310 utilizing the user interface 142. Based on the user selections received by the controller circuit 102 via the user interface 142, the controller circuit 102 may select the models 109 of the group 310.

At 222, the controller circuit 102 is configured to perform a first diagnostic procedure of the anatomical structure of interest based on the first model. For example, the first diagnostic procedure may be configured to calculate dimensions of the left ventricle of the heart. Based on a size of the chamber 404 of the medical image 400 (FIG. 4) is larger relative to the remaining chambers 406-410, the controller circuit 102 may determine by executing the first model that the chamber 404 corresponds to the left ventricle. Based on the spatial position of the adjacent chambers 406-410 to the chamber 404 and within the ultrasound image 400, the controller circuit 102 may classify the chamber 406-410. For example, since the chamber 406 is positioned adjacent and approximately parallel along a horizontal axis to the chamber 404, the controller circuit 102 may classify the chamber 406 as the right ventricle. In another example, since the chamber 410 is centrally positioned within the ultrasound image 400 and/or is adjacent to all of the chambers 404-408, the controller circuit 102 may classify the chamber 410 as the aortic valve. The controller circuit 102 may be configured to identify a boundary of the chamber 404 based on changes in pixel intensities and/or shape features based on the executed first model. Based on the identified boundary of the chamber 404, the controller circuit 102 may calculate a distances between opposing ends of the boundary to determine dimensions of the left ventricle (e.g., the chamber 404). It may be noted that the controller circuit 102 may be configured to execute more than one model concurrently and/or simultaneously when executing the first model.

At 224, the controller circuit 102 is configured to update the first model based on an adjustment to the first diagnostic procedure. The controller circuit 102 may be configured to receive an adjustment to the diagnostic procedure based on a user selection, and adjust the first model based on the adjustment to the first diagnostic procedure. For example, the controller circuit 102 may calculate the dimensions of the anatomical structure of interest based on the identified boundaries identified by the controller circuit executing the first model. The user may adjust the boundary and/or the dimensions utilizing the user interface 142. Based on the adjustment, the controller circuit 102 may execute the machine learning algorithm 107 to update the first model.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A computer implemented method, comprising:
    organizing a plurality of models into a hierarchical structure based on anatomical structures, wherein the plurality of models are defined by a machine learning algorithm for diagnostic procedures of one or more of the anatomical structures;
    receiving a medical image;
    identifying an anatomical structure of interest within the medical image;
    selecting at least a first model from the plurality of models based on the anatomical structure of interest; and
    performing a first diagnostic procedure of the anatomical structure of interest based on the first model.

2. The computer implemented method of claim 1, wherein the first diagnostic procedure is at least one of identifying a two-dimensional plane, segmenting the anatomical structure of interest, measuring a boundary thickness of the anatomical structure of interest, measuring a volume of the anatomical structure of interest, identifying the anatomical structure within the medical image, annotating objects within the medical image, or measuring an area of the anatomical structure of interest.

3. The computer implemented method of claim 1, wherein the first model is selected based on a user selection.

4. The computer implemented method of claim 1, wherein the medical image is based on ultrasound data acquired from an ultrasound probe.

5. The computer implemented method of claim 1, wherein the medical image is received based on a selection of the medical image from a set of medical images acquired by a medical diagnostic imaging system.

6. The computer implemented method of claim 1, further comprising receiving an adjustment to the first diagnostic procedure, and adjusting the first model based on the adjustment to the first diagnostic procedure.

7. The computer implemented method of claim 1, wherein the anatomical structures include at least one of a heart, a bone, a brain, a head, a bladder, a kidney, a liver, or a vein.

8. A medical diagnostic imaging system comprising:
    a display configured to display one or more medical images; and
    a controller circuit configured to:
        organize a plurality of models into a hierarchical structure based on anatomical structures, wherein the plurality of models are defined by a machine learning algorithm for diagnostic procedures of one or more of the anatomical structures;
        receive a medical image;
        identify an anatomical structure of interest within the medical image;
        select at least a first model from the plurality of models based on the anatomical structure of interest; and
        perform a first diagnostic procedure of the anatomical structure of interest based on the first model.

9. The medical diagnostic imaging system of claim 8, wherein the first diagnostic procedure is at least one of identifying a two-dimensional plane, segmenting the anatomical structure of interest, measuring a boundary thickness of the anatomical structure of interest, measuring a volume of the anatomical structure of interest, identifying the anatomical structure within the medical image, annotating objects within the medical image, or measuring an area of the anatomical structure of interest.

10. The medical diagnostic imaging system of claim 8, further comprising a user interface, wherein the first model is selected based on a user selection.

11. The medical diagnostic imaging system of claim 8, further comprising an ultrasound probe having a plurality of transducer elements, the controller circuit is further configured to acquire ultrasound data from the ultrasound probe, and wherein the receiving the medical image includes generating the medical image based on the ultrasound data.

12. The medical diagnostic imaging system of claim 8, further comprising a user interface, wherein the medical image is received based on a selection of the medical image from a set of medical images based on a user selection.

13. The medical diagnostic imaging system of claim 8, further comprising a user interface, wherein the controller circuit is configured to receive an adjustment to the first diagnostic procedure based on a user selection, and adjust the first model based on the adjustment to the first diagnostic procedure.

14. The medical diagnostic imaging system of claim 8, wherein the anatomical structures include at least one of a heart, a bone, a brain, a head, a bladder, a kidney, a liver, or a vein.

15. A tangible and non-transitory computer readable medium comprising one or more programmed instructions configured to direct one or more processors to:
    organize a plurality of models into a hierarchical structure based on anatomical structures, wherein the plurality of models are defined by a machine learning algorithm for diagnostic procedures of one or more of the anatomical structures;

receive a medical image;
identify an anatomical structure of interest within the medical image;
select at least a first model from the plurality of models based on the anatomical structure of interest; and
perform a first diagnostic procedure of the anatomical structure of interest based on the first model.

16. The tangible and non-transitory computer readable medium of claim 15, wherein the first diagnostic procedure is at least one of identifying a two-dimensional plane, segmenting the anatomical structure of interest, measuring a boundary thickness of the anatomical structure of interest, measuring a volume of the anatomical structure of interest, identifying the anatomical structure within the medical image, annotating objects within the medical image, or measuring an area of the anatomical structure of interest.

17. The tangible and non-transitory computer readable medium of claim 15, wherein the first model is selected based on a user selection.

18. The tangible and non-transitory computer readable medium of claim 15, wherein the medical image is based on ultrasound data acquired from an ultrasound probe.

19. The tangible and non-transitory computer readable medium of claim 15, wherein the medical image is received based on a selection of the medical image from a set of medical images acquired by a medical diagnostic imaging system.

20. The tangible and non-transitory computer readable medium of claim 15, wherein the anatomical structures include at least one of a heart, a bone, a brain, a head, a bladder, a kidney, a liver, or a vein.

\* \* \* \* \*